(12) United States Patent
Kajanto (10) Patent No.: US 11,555,079 B2
(45) Date of Patent: *Jan. 17, 2023

(54) PROCESS FOR PRODUCING AN OXIDIZED NANOFIBRILLAR CELLULOSE HYDROGEL

(71) Applicant: UPM-KYMMENE CORPORATION, Helsinki (FI)

(72) Inventor: Isko Kajanto, Espoo (FI)

(73) Assignee: UPM-KYMMENE CORPORATION, Helsinki (FI)

( * ) Notice: Subject to any disclaimer, the term of this patent is extended or adjusted under 35 U.S.C. 154(b) by 53 days.

This patent is subject to a terminal disclaimer.

(21) Appl. No.: 15/538,082

(22) PCT Filed: Dec. 21, 2015

(86) PCT No.: PCT/FI2015/050919
§ 371 (c)(1),
(2) Date: Jun. 20, 2017

(87) PCT Pub. No.: WO2016/102767
PCT Pub. Date: Jun. 30, 2016

(65) Prior Publication Data
US 2017/0349671 A1 Dec. 7, 2017

(30) Foreign Application Priority Data
Dec. 22, 2014 (FI) .................................. 20146135

(51) Int. Cl.
| C08B 15/04 | (2006.01) |
| A61K 8/02 | (2006.01) |
| A61K 8/73 | (2006.01) |
| A61K 9/70 | (2006.01) |
| A61K 47/38 | (2006.01) |
| A61Q 19/00 | (2006.01) |
| D01F 2/24 | (2006.01) |
| D21H 11/18 | (2006.01) |
| D21H 11/20 | (2006.01) |

(52) U.S. Cl.
CPC ............. *C08B 15/04* (2013.01); *A61K 8/027* (2013.01); *A61K 8/731* (2013.01); *A61K 9/70* (2013.01); *A61K 47/38* (2013.01); *A61Q 19/00* (2013.01); *D01F 2/24* (2013.01); *D21H 11/18* (2013.01); *D21H 11/20* (2013.01); *A61K 2800/10* (2013.01)

(58) Field of Classification Search
CPC ........ C08B 15/04; A61K 47/38; A61K 31/717

USPC ......................................................... 536/124
See application file for complete search history.

(56) References Cited

U.S. PATENT DOCUMENTS

| 4,850,270 A * | 7/1989 | Bronnert | A23L 3/22 |
| | | | 99/355 |
| 9,631,177 B2 * | 4/2017 | Yliperttula | A61K 9/06 |
| 9,797,093 B2 * | 10/2017 | Laukkanen | C08B 15/00 |
| 9,833,540 B2 * | 12/2017 | Laukkanen | A61L 15/28 |
| 2007/0010153 A1 * | 1/2007 | Shaffer | A47L 13/16 |
| | | | 15/208 |

FOREIGN PATENT DOCUMENTS

| WO | WO-0033893 A1 * | 6/2000 | ............ A61L 15/32 |
| WO | 2012168562 | 12/2012 | |
| WO | 2013072563 | 5/2013 | |
| WO | 2013093199 | 6/2013 | |

OTHER PUBLICATIONS

Chinga-Carrasco et al, Journal of Biomaterials Applications, "Pretreatment-dependent surface chemistry of wood nanocellulose for pH-sensitive hydrogels", vol. 29, No. 3, 2014.
Borges et al, "Nanofibrillated cellulose composite hydrogel for the replacement of the nucleus pulposus", Acta Biomaterialia, vol. 7, No. 9, 2011.
Search Report, FI Patent Application No. 20146135, dated Apr. 21, 2015.
International Search Report, PCT Application No. PCT/FI2015/050919, dated Feb. 24, 2016.
Liljestrom, A., "Cell Adhesion on Cellulose Nanofibrils," Master's thesis for the degree of Master of Science in Bioproduct Technology, Aalto University School of Chemical Technology, Espoo, Finland, Oct. 30, 2015.
Communication under Rule 71(3) in European Patent Application No. EP 15828500.7, dated May 23, 2022 (5 pages).

* cited by examiner

*Primary Examiner* — Leigh C Maier
*Assistant Examiner* — Everett White (57) ABSTRACT

A process for producing an oxidized nanofibrillar cellulose hydrogel is disclosed, wherein the process comprises oxidizing cellulose pulp fibers in the presence of hypochlorite as an oxidant and a heterocyclic nitroxyl radical as a catalyst; and disintegrating the oxidized cellulose pulp fibers to obtain a nanofibrillar cellulose hydrogel; wherein all steps of the process after oxidizing are performed under aseptic conditions. An oxidized nanofibrillar cellulose hydrogel and a system for producing the same are also disclosed.

11 Claims, 2 Drawing Sheets

PROCESS FOR PRODUCING AN OXIDIZED NANOFIBRILLAR CELLULOSE HYDROGEL

CROSS-REFERENCE TO RELATED APPLICATIONS

This application is a U.S. National Stage of International Application No. PCT/FI2015/050919, filed on Dec. 21, 2015, which claims priority to Finnish Patent No. 20146135, filed Dec. 22, 2014, the contents of each of which are incorporated herein by reference in their entireties.

FIELD OF THE INVENTION

The invention relates to a process for producing an oxidized nanofibrillar cellulose hydrogel, an oxidized nanofibrillar cellulose hydrogel, its uses and a system for producing the same.

BACKGROUND

Nanofibrillar cellulose hydrogel has found use in various applications, such as in cosmetics, pharmaceuticals and as a growth medium for cell culture. However, such uses typically require that the hydrogel is aseptic or sterile. Yet other properties of the hydrogel should not be affected by the sterilization.

Generally, sterilization efficiency is defined as the ability to remove or destroy all forms of microbial life, including viruses, bacteria and fungi, as vegetative forms or spores. However, since absolute sterility cannot be verified, a statistical definition of sterility is used in practice. For instance, the security assurance level (SAL) is defined as "the probability of a single viable micro-organism occurring in or on a product after sterilization". The worldwide accepted definition of sterility of medical devices is defined as the chance of finding a viable organism in or on a medical device to be at most 1 in 1000000 or a SAL of at most $10^{-6}$.

The number of viable micro-organisms in nanofibrillar cellulose hydrogel can be reduced or eliminated e.g. by subjecting the hydrogel to autoclaving for 20 minutes at a temperature of 121° C. Autoclaving, however, has some drawbacks, as it may affect the properties, such as viscosity, of the hydrogel, in particular of anionic (oxidized) nanofibrillar cellulose hydrogel.

The inventors have therefore recognized the need for a process of producing oxidized nanofibrillar cellulose hydrogel such that it is suitable for further applications.

PURPOSE OF THE INVENTION

The purpose of the invention is to provide a new type of process for producing an oxidized nanofibrillar cellulose hydrogel. Further, the purpose of the invention is to provide a new type of oxidized nanofibrillar cellulose hydrogel and new uses of the oxidized nanofibrillar cellulose hydrogel. Further, the purpose of the invention is to provide a new system for producing an oxidized nanofibrillar cellulose hydrogel.

SUMMARY

A process for producing an oxidized nanofibrillar cellulose hydrogel includes oxidizing cellulose pulp fibers in the presence of hypochlorite as an oxidant and a heterocyclic nitroxyl radical as a catalyst to form sterile or essentially sterile oxidized cellulose pulp fibers, wherein a total amount of hypochlorite ions fed is at least 2.0 mmol/g based on dry weight of the cellulose pulp fibers, and wherein the oxidizing is conducted for 1 to 8 hours, wherein hypochlorite ions are present during at least a period of time during the oxidizing at a concentration level of 0.5 to 5.0 g/l, the concentration level being calculated based on the total volume of a mixture of the hypochlorite ions, the cellulose pulp fibers, and an aqueous solution in which the oxidizing takes place The process further includes adjusting the concentration of the oxidized cellulose pulp fibers to equal to or less than 3% (w/w). The process further includes disintegrating the oxidized cellulose pulp fibers to obtain a sterile or essentially sterile oxidized nanofibrillar cellulose hydrogel having a viscosity of at least 2000 mPa·s, as measured at a 0.8% (w/w) concentration of the nanofibrillar cellulose in water with a Brookfield viscometer at a temperature of 20°C, with a vane spindle and a measuring speed of 10 rpm. The oxidized cellulose pulp fibers are continuously transported from one process step to a next process step in a closed environment using an aseptic connection, the aseptic conditions including using components of a system for producing the oxidized nanofibrillar cellulose hydrogel that are configured to be in contact with the oxidized cellulose pulp fibers and/or oxidized nanofibrillar cellulose that are decontaminated and provide uncompromised, continuous isolation of their interior from the external environment. All steps of the process after the adjusting step are performed under aseptic conditions, the conditions including meeting a cleanroom classification, according to ISO 14644-1 cleanroom standards, of at least Class ISO 8.

BRIEF DESCRIPTION OF THE DRAWINGS

The accompanying drawings, which are included to provide a further understanding of the invention and constitute a part of this specification, illustrate embodiments of the invention and together with the description help to explain the principles of the invention. In the drawings.

DETAILED DESCRIPTION

A process for producing an oxidized nanofibrillar cellulose hydrogel is disclosed, comprising
oxidizing cellulose pulp fibers in the presence of hypochlorite as an oxidant and a heterocyclic nitroxyl radical as a catalyst; and
disintegrating the oxidized cellulose pulp fibers to obtain an oxidized nanofibrillar cellulose hydrogel;
wherein all steps of the process after oxidizing are performed under aseptic conditions.

During the oxidizing, a proportion of the hydroxyl (OH) groups of the cellulose pulp fibers are oxidized into carboxyl (COOH) groups. When subsequently disintegrating the oxidized cellulose pulp fibers, they disintegrate more readily than native cellulose pulp fibers, i.e. cellulose pulp fibers that have not been oxidized, therefore resulting in smaller fibrils and subsequently a less turbid nanofibrillar cellulose hydrogel. The oxidized nanofibrillar cellulose is also commonly referred to as anionic oxidized nanofibrillar cellulose. The cellulose pulp fibers may be dispersed in an aqueous solution, such as water, for the oxidizing.

The expression "nanofibrillar cellulose" or "NFC" should be understood in this specification, unless otherwise stated, as referring to a collection of isolated cellulose nanofibrils (CNF) and/or nanofibril bundles derived from a cellulose-based raw material.

Nanofibrils typically have a high aspect ratio. The length might exceed one micrometer while the diameter is typically below 200 nm. The smallest nanofibrils are similar to so called elementary fibrils, which are typically approx. 2-12 nm in diameter. The dimensions of the fibrils or fibril bundles are dependent on the raw material and the disintegration method. Fibrils of the oxidized NFC have typically smaller diameters, the number average diameter ranging from 1 to 100 nm, or 2 to 20 nm, or 2 to 10 nm. The diameter of a fibril may be determined with several techniques, such as by using a microscope. Fibril thickness and width distribution may be measured by image analysis of images from a field emission scanning electron microscope (FE-SEM), a transmission electron microscope (TEM), such as a cryogenic transmission electron microscope (cryo-TEM), or an atomic force microscope (AFM). In general, AFM and TEM suit NFC grades with narrow fibril diameter distribution best.

Cellulose pulp fibers may be obtained from a cellulose-based raw material. The expression "cellulose-based raw material" should be understood in this specification, unless otherwise stated, as referring to any raw material source that contains cellulose and from which cellulose pulp fibers, and subsequently nanofibrillar cellulose, can be produced.

The cellulose-based fiber material may, in principle, be based on any plant material that contains cellulose. The plant material may be wood. Wood can be from a softwood tree such as spruce, pine, fir, larch, douglas-fir or hemlock, or from a hardwood tree such as birch, aspen, poplar, alder, eucalyptus or acacia, or from a mixture of softwoods and hardwoods. Non-wood material may be derived from agricultural residues, grasses or other plant substances such as straw, leaves, bark, seeds, hulls, flowers, vegetables or fruits from cotton, corn, wheat, oat, rye, barley, rice, flax, hemp, manila hemp, sisal hemp, jute, ramie, kenaf, bagasse, bamboo or reed. Depending on the raw material source, e.g. hardwood (HW) vs. softwood (SW) pulp, different polysaccharide compositions may exist in the final NFC product. The nanofibrillar celluloses may contain hemicelluloses and lignin in varying amounts, depending on plant source and pulping conditions. For example, bleached birch pulp has a high xylose content (25% by weight) and a negligible lignin content. The nanofibrillar celluloses are always complex mixtures of different polysaccharide structures.

The cellulose-based fiber material may be formed by isolating cellulose fibers from a raw material that contains cellulose by chemical, mechanical, thermo-mechanical, or chemi-thermo-mechanical pulping processes, for example kraft pulping, sulfate pulping, soda pulping, organosols pulping, and by conventional bleaching processes. The cellulose-based fiber material may not contain substantial amounts of lignin, or it may contain only traces of lignin or non-detectable amounts of lignin. Thus also the NFC may be essentially lignin-free.

Nanofibrillar cellulose is characterized by very high water retention values, a high degree of chemical accessibility and the ability to form stable gels, hydrogels, in water or other polar solvents. A nanofibrillar cellulose product is typically a dense network of highly fibrillated cellulose. In an aqueous environment, a dispersion of cellulose nanofibers forms a viscoelastic hydrogel network. The hydrogel is formed at relatively low concentrations, for example 0.05-0.2% (w/w), of dispersed and hydrated entangled fibrils.

The cellulose pulp comprises both crystalline and amorphous regions in the cellulose. The crystallinity of the cellulose pulp used as the starting material may be at least 50%. Suitably the crystallinity of the cellulose pulp is at least 55%, such as at least 60%, or at least 65%, or at least 70%. Examples of suitable crystallinity values of the NFC include from 50 to 85%, such as from 60% to 80%, or from 65 to 75%. The NFC consists essentially of cellulose I.

The expression "hydrogel" or "nanofibrillar cellulose hydrogel" should be understood in this specification, unless otherwise stated, as referring to an aqueous dispersion of nanofibrillar cellulose having a continuous or discontinuous gel structure. The hydrogel can be formed by combining nanofibrillar cellulose with e.g. water, buffer solution, cell culture medium or any other aqueous solution optionally supplemented with additives. The storage modulus (G') value of the hydrogel of nanofibrillar cellulose is greater than its loss modulus (G") value, the ratio of these, the loss tangent (G"/G'), being less than 1 at least up to strain value 10%.

The viscoelastic properties storage modulus G', loss modulus G" and loss tangent (G"/G') of the NFC hydrogels may be determined with the frequency sweep in dynamic oscillation mode of the rheometer (strain 1% and 10%, frequency 0.1-100, temperature 25° C., pH 7.0). The stress sweep is measured in a shear stress range of 0.001-100 Pa at the frequency 0.1 Hz, at 25° C., pH 7. For characterizing the gel forming capacity of a nanofibrillar cellulose grade the measurement is performed in 0.5 wt %, 1% strain, frequency of 0.1 Hz. For determining whether a certain material is a gel, i.e. whether its loss tangent is <1, the measurement is performed in the same way except in the consistency of the material (i.e. the material is not diluted prior to measurement). The storage modulus of oxidized nanofibrillar celluloses may vary from 1 to 100 Pa, and typically the storage modulus varies from 2 to 50 Pa, or 5 to 20 Pa, in water at 0.5 wt % concentration.

The process may be a process for producing a sterile or essentially sterile oxidized nanofibrillar cellulose hydrogel.

The expression "sterile" may be understood in this specification, unless otherwise stated, to refer to a nanofibrillar cellulose hydrogel or other substance, material, composition or component that is essentially free of viable micro-organisms. Because it is, in practice, very difficult to demonstrate that the nanofibrillar cellulose hydrogel would in fact be absolutely sterile, the sterility may be defined on the basis of measurement of the number of viable micro-organisms present in the nanofibrillar cellulose hydrogel by measuring the number of colony forming units.

In the context of this specification, the term "colony forming unit" or "CFU" should, as it is commonly used in microbiology, be understood as a measure or estimate of the number of viable micro-organisms in a sample. It corresponds to the formation of a single macroscopic colony after the introduction of one or more micro-organisms to microbiological growth media. Means and methods for estimating colony forming units are well known in microbiology. The presence of viable micro-organisms in the nanofibrillar cellulose hydrogel can be determined by culturing on a growth medium. Several protocols for determining the number of colony forming units are available.

In an embodiment, the number of colony-forming units per gram of nanofibrillar cellulose hydrogel is determined by preparing a dilution series of the hydrogel and by plating the dilution series on separate Petrifilm plates (3M) for aerobic bacteria (aerobic plate count) and for yeasts and moulds. The plates for aerobic bacteria are allowed to grow at 37° C. for 2 days and the plates for yeasts and moulds at 30° C. for 3-5 days, after which the colonies are counted. The number of colony-forming units of aerobic heterotrophs are determined by culturing the sample on plate count agar at a temperature of 37° C. for three (3) days. Alternatively, the presence of yeasts and/or fungi can be determined by culturing on potato dextrose agar at a temperature of 25° C. for five (5) days. Before the measurement, the samples are diluted ten-fold. The presence of anaerobic micro-organisms can be determined by culturing on brewer anaerobic agar for anaerobic bacterial count at a temperature of 30° C. for three (3) days in anaerobic conditions. Before the measurement, the samples are diluted ten-fold.

In an embodiment, the number of colony-forming units is determined by following the standard ISO 8784-1 (Pulp, Paper and board—Microbiological examination. Part 1: Total count of bacteria, yeast and mould based on disintegration). The results are given as the number of colony-forming units per gram of the sample.

In an embodiment, the number of colony-forming units of viable micro-organism per gram of nanofibrillar cellulose hydrogel may be measured by incubating at 37° C. for 14 days following the USP XXIV Chapter 71 sterility test.

Sterile nanofibrillar cellulose hydrogel may comprise fewer than 1 CFU, or fewer than $10^{-1}$ CFU, or fewer than $10^{-2}$ CFU, or fewer than $10^3$ CFU, or fewer than $10^{-4}$ CFU, or fewer than $10^{-5}$ CFU, or fewer than $10^{-6}$ CFU of a viable micro-organism per unit of the nanofibrillar cellulose hydrogel. The term "a viable micro-organism" may refer to one or more viable micro-organisms of the same or different species or strains. In other words, if the nanofibrillar cellulose hydrogel comprises fewer than $10^{-6}$ CFU of a viable micro-organism per unit of the nanofibrillar cellulose hydrogel, there is a probability of not more than one viable micro-organism in one million units of the nanofibrillar cellulose hydrogel; or less than one produced unit of the oxidized nanofibrillar cellulose hydrogel in a million is exposed to the risk of not being absolutely sterile. The unit may be one gram of the oxidized nanofibrillar cellulose hydrogel. The unit may also be a package containing 1 g, 5 g or 10 g of oxidized nanofibrillar cellulose hydrogel. The unit may further be a multiwell plate containing oxidized nanofibrillar cellulose hydrogel in one or more wells or a single well of a multiwell plate containing oxidized nanofibrillar cellulose hydrogel.

Sterile nanofibrillar cellulose hydrogel may thus comprise fewer than 1 CFU, or fewer than $10^{-1}$ CFU, or fewer than $10^{-2}$ CFU, or fewer than $10^3$ CFU, or fewer than $10^{-4}$ CFU, or fewer than $10^{-5}$ CFU, or fewer than $10^{-6}$ CFU of a viable micro-organism per gram of the nanofibrillar cellulose hydrogel. In other words, if the nanofibrillar cellulose hydrogel comprises fewer than $10^{-6}$ CFU of a viable micro-organism per gram of the nanofibrillar cellulose hydrogel, there is a probability of not more than one viable micro-organism in one million grams of the nanofibrillar cellulose hydrogel.

The degree of sterility of the oxidized nanofibrillar cellulose hydrogel that is required may depend e.g. on its intended use.

In the context of this specification, the term "sterilization" or "sterilization process" may refer to any physical or chemical process capable of destroying all life forms and micro-organisms in particular and of inactivating viruses. A sterilization treatment or process may destroy life forms to a varying extent depending on the conditions and the micro-organism. For instance, autoclaving at a temperature of about 121° C. and at high pressure for a time period of about 15-20 minutes is typically a quite effective sterilization process and may be capable of reducing the number of viable micro-organisms by a factor of at least $10^{12}$.

The present inventors have found that oxidizing cellulose pulp fibers in the presence of hypochlorite as an oxidant and a heterocyclic nitroxyl radical as a catalyst results in a significant reduction of the number of viable micro-organisms in the reaction mixture. As the oxidized cellulose pulp fibers contain a low number of viable micro-organisms or are essentially sterile, an essentially sterile oxidized nanofibrillar cellulose hydrogel may be obtained, if all steps of the process after the oxidizing are performed under aseptic conditions. The aseptic conditions should be such that viable micro-organisms are not introduced into the oxidized cellulose fibers and/or oxidized nanofibrillar cellulose hydrogel during the process.

In the context of this specification, the aseptic conditions may include performing all steps of the process after the oxidizing in an environment that has a controlled level of contamination by micro-organisms and particles, such as a cleanroom or a building, or a segregated segment of it, containing an aseptic processing room in which air supply, materials, and equipment are regulated to control microbial and particle contamination. Aseptic conditions may, throughout this specification, refer to the conditions in an aseptic processing room assigned to and reproducibly meeting a cleanroom classification (ISO 14644-1 cleanroom standards) of at least Class ISO 8, or at least ISO 7, or at least ISO 6, or at least ISO 5, or at least ISO 4, or at least ISO 3, or at least ISO 2, or ISO 1. The aseptic conditions may also correspond to ISO 14644-1 cleanroom standard ISO 5, or to ISO 4, or to ISO 3, or to ISO 2, or to ISO 1. The environment that has a controlled level of contamination by micro-organisms and particles is designed or adapted, maintained, and controlled to prevent particle and microbiological contamination of the oxidized cellulose fibers and/or oxidized nanofibrillar cellulose hydrogel being processed after the oxiding. Ventilation air to the environment may be e.g. filtered. The requirements for the environment may depend on other conditions of the process—for instance, if the process is not fully closed, higher requirements for microbial and particle contamination may be used for the environment.

In the context of this specification, the aseptic conditions may also include using aseptic techniques of working and of handling the oxidized cellulose fibers and/or oxidized nanofibrillar cellulose hydrogel and any material that is to be in contact with the oxidized cellulose fibers and/or oxidized nanofibrillar cellulose hydrogel.

After oxidizing, the following process steps may be performed in a closed environment so that the oxidized cellulose pulp fibers and/or the oxidized nanofibrillar cellulose hydrogel is transported from one process step to the next using aseptic connections, such as pipelines.

In the context of this specification, the aseptic conditions may also include using components, such as containers, reactors, pumps and connections, of a system for producing the oxidized nanofibrillar cellulose hydrogel that are configured to be in contact with the oxidized cellulose pulp fibers and/or oxidized nanofibrillar cellulose that are decontaminated, e.g. sterilized. Said components may provide uncompromised, continuous isolation of their interior from the external environment.

The aseptic conditions may also include using reagents or additives, such as water used for washing or diluting the oxidized cellulose pulp fibers and/or the oxidized nanofibrillar cellulose hydrogel, that are in contact with or added to the oxidized cellulose pulp fibers and/or the oxidized nanofibrillar cellulose hydrogel, that are sterilized. Said reagents or additives may be sterile or essentially sterile. For instance, autoclaved water may be used.

Said all steps of the process after the oxidizing include disintegrating the oxidized cellulose pulp fibers to obtain an oxidized nanofibrillar cellulose hydrogel. They may also include any subsequent optional processing steps, such as further sterilization treatment and packaging steps of the oxidized nanofibrillar cellulose hydrogel.

The hypochlorite ion is an ion composed of chlorine and oxygen, with the chemical formula $ClO^-$. It can combine with a number of counter-ions to form hypochlorites, which may also be regarded as salts of hypochlorous acid. A hypochlorite is therefore a chemical compound containing the hypochlorite ion and a counter-ion, such as sodium or calcium. The hypochlorite may be sodium hypochlorite (NaClO). It may also be calcium hypochlorite ($Ca(ClO)_2$).

The heterocyclic nitroxyl radical included as a catalyst may be any heterocyclic nitroxyl radical capable of catalyzing selectively the oxidation of hydroxyl groups of the C-6 carbon of cellulose, for example 2,2,6,6-tetramethylpiperidinyl-1-oxy free radical (TEMPO). Various TEMPO oxidation processes for cellulose are known in the art. Other heterocyclic nitroxyl compounds known to display selectivity in the oxidation of the hydroxyl groups of the C-6 carbon of cellulose are known and may also be included as a catalyst.

Hypochlorite functions as the main oxidant during the oxidizing. Other components or additives may also be included, such as an activator that is capable of accelerating the reaction. Suitable activators may be e.g. sodium bromide (NaBr) and other bromide compounds, chlorine dioxide or a tertiary amine. The hypochlorite itself (e.g. NaClO) may also function as the activator. The activation may be performed prior to the addition of the cellulose pulp fibers and the actual oxidizing in order to accelerate the start of the oxidizing process.

The temperature during the oxidizing may be e.g. in the range of 20 to 50° C. As the catalytic oxidizing is exothermic, the temperature during the oxidizing also tends to rise. The temperature during the oxidizing may be raised to at least 30° C., or to at least 35° C., or to at least 40° C. At higher temperatures, the number of viable micro-organisms may be reduced more efficiently during oxidizing.

The process may comprise oxidizing cellulose pulp fibers in the presence of hypochlorite as an oxidant and a heterocyclic nitroxyl radical as a catalyst at a pH of at least 7, or at least 8, or at least 8.5, or 7-10, or 8.5-9. The alkaline environment facilitates the oxidation efficiently; further, micro-organisms may be susceptible to alkaline pH.

Hypochlorite ions may be present during at least a period of time during the oxidizing at a concentration level of at least 0.5 g/l or at a concentration in the range of 0.5-5 g/l. This concentration is calculated on the basis of the total volume of the mixture of hypochlorite, cellulose pulp fibers and an aqueous solution in which the oxidizing takes place. Hypochlorite ions may be present at said concentration level during the whole oxidizing process or only a period of time during the oxidizing, for instance for a period of time of about 0.5 h-1 h within the oxidizing process or during a pulse of hypochlorite being fed into the oxidizing process.

The concentration of hypochlorite ions may depend e.g. on the amount of cellulose pulp fibers in the oxidization mixture in an aqueous solution. The concentration (w/w) of hypochlorite ions that is required in the reaction may be calculated using the following formula $$c_h = m_h \cdot \frac{N_h}{w_{pulp}} \cdot \frac{w_{pulp}}{w_{H2O}} = m_h \cdot \frac{N_h}{w_{pulp}} \cdot c_{pulp}$$

wherein
$m_h$ is the molecular weight of the hypochlorite ion;
$N_h$ is the number of hypochlorite ions in moles;
$w_{pulp}$ is the weight of cellulose pulp fibers;
$w_{H2O}$ is the weight of the aqueous solution; and
$c_{pulp}$ is the concentration (w/w) of pulp in aqueous solution.

The molarity $M_h$ of the hypochlorite ions that are required in the reaction may also be calculated using the following formula:

$$M_h = \frac{N_h}{w_{pulp}} \cdot c_{pulp}$$

wherein
$N_h$ is the number of hypochlorite ions in moles;
$w_{pulp}$ is the weight of cellulose pulp fibers; and
$c_{pulp}$ is the concentration (w/w) of pulp in the aqueous solution.

In these formulae, the parameter $N_h/w_{pulp}$ corresponds to the concentration of hypochlorite ions based on the dry weight of the cellulose pulp fibers.

In practice, hypochlorite may be fed into the oxidizing process as a single pulse at the beginning of the oxidizing. Hypochlorite may also be fed into the oxidizing process continuously by feeding a first pulse of hypochlorite at the beginning of the oxidizing, a second pulse later on during the oxidizing and by feeding hypochlorite at a lower level, for instance at a constant rate, between the first and second pulse and after the second pulse. The hypochlorite may be fed e.g. so that the first pulse fed at the beginning of the oxidizing process may comprise approx. 50-67% of all hypochlorite fed into the oxidizing process and the remaining hypochlorite is fed at a lower level, for instance at a constant rate, with an optional, smaller second pulse. Hypochlorite may also be fed continuously, for instance at a constant rate. Regardless of the manner of feeding the hypochlorite, if hypochlorite ions are present during at least a period of time during the oxidizing at a concentration level of at least 0.5 g/l, or 0.5 to 5.0 g/l, the concentration of hypochlorite may be particularly efficient in reducing the number of viable micro-organisms.

The total amount of hypochlorite ions fed may be at least 2.0 mmol/g, or at least 2.4 mmol/g, based on dry weight of the cellulose pulp fibers. Such concentrations may allow for an oxidation level that is sufficient for efficient disintegration of the oxidized cellulose pulp fibers. Such concentrations may also be sufficient for reducing the number of viable micro-organisms.

The total amount of hypochlorite ions fed (i.e. the total amount of hypochlorite ions fed in the oxidizing process) may also be in the range of 2.0-5.0 mmol/g based on dry weight of the cellulose pulp fibers. Such amounts provide oxidized nanofibrillar cellulose that is still substantially insoluble; very high amounts of hypochlorite ions may lead to the oxidized nanofibrillar cellulose being at least partially soluble in water.

The concentration level and the total amount of hypochlorite ions fed may also depend e.g. on the consistency of the cellulose pulp fibers, which may be e.g. in the range of 1%-10% (w/w). In one embodiment the consistency of the cellulose pulp fibers subjected to oxidizing is at least 3% (w/w) and the total amount of hypochlorite ions fed is at least 2.0 mmol/g based on dry weight of the cellulose pulp fibers. In this embodiment hypochlorite ions are present during at least a period of time during the oxidizing at a concentration level of at least 0.5 g/l. A skilled person is able to determine the amount or concentration of hypochlorite required depending on the various parameters described herein.

When the total amount of hypochlorite ions fed is at least 2.0 mmol/g, or in the range of 2.0-5.0 mmol/g, the concentration of the cellulose pulp fibers may be at least 3% (w/w).

The concentration level and the total amount of hypochlorite ions fed may also depend e.g. on the consistency of the cellulose pulp fibers, which may be e.g. in the range of 1%-10% (w/w). A skilled person is able to determine the amount or concentration of hypochlorite required depending on the various parameters described herein.

The cellulose pulp fibers may be oxidized to an oxidation level (conversion degree) of at least about 500 μmol/g, or at least about 800 μmol/g, or about 500-1500 μmol/g, or about 800-1200 μmol/g of COOH residues based on the dry weight of the pulp.

The oxidation level (conversion degree) of about 500 μmol/g may be achieved e.g. by using hypochlorite ions at a total amount of 1.8 mmol/g; 1500 μmol/g by using hypochlorite ions at a total amount of 9 mmol/g; 800 μmol/g using hypochlorite ions at a total amount of 2.9 mmol/g; and 1200 μmol/g using hypochlorite ions at a total amount of 6 mmol/g based on the dry weight of the cellulose pulp fibers.

In an example, for an oxidizing process in which cellulose pulp fibers are present at a concentration of 4% (w/w) and hypochlorite is fed so that the first pulse fed at the beginning of the oxidizing process may comprise approx. 50-67% of all hypochlorite fed into the oxidizing process and the remaining hypochlorite is fed at a constant level, with an optional, smaller second pulse, the cellulose pulp fibers are oxidized to an oxidation level about 800 μmol/g and hypochlorite ions are present for about half of the duration of the oxidizing at a concentration level of at least 0.5 g/l. The duration of the oxidizing may be about 2.5 h. In such an example, the maximum instantaneous concentration level of hypochlorite ions may be 1.25 g/l.

In an example, for an oxidizing process in which cellulose pulp fibers are present at a concentration of 4% (w/w) and hypochlorite is fed so that the first pulse fed at the beginning of the oxidizing process may comprise approx. 50-67% of all hypochlorite fed into the oxidizing process and the remaining hypochlorite is fed at a constant level, with an optional, smaller second pulse, the cellulose pulp fibers are oxidized to an oxidation level of at least 1000 μmol/g and hypochlorite ions are present for the entire duration of the oxidizing at a concentration level of at least 0.5 g/l. The duration of the oxidizing may be about 2.5 h. In such an example, the maximum instantaneous concentration level of hypochlorite ions may be 3 g/l.

The oxidizing may be conducted for at least 1 h, or at least 2 h, or 1 to 8 h, or 2 to 5 h. The longer the contact time with hypochlorite, the more efficient is the micro-organism reducing effect of the oxidizing. The number of viable micro-organisms may be reduced by a factor of 10 for each 5 min of treatment for at least some micro-organisms; 1 h of oxidizing may therefore be able to reduce the number of at least some viable micro-organisms by as much as a factor of $10^{12}$. Commonly used oxidizing times of about 2 hours or longer may therefore be very efficient in reducing the number of viable micro-organisms.

The process may further comprise washing the oxidized cellulose pulp fibers prior to disintegrating. The process may also comprise adjusting the concentration of the oxidized cellulose pulp fibers prior to disintegrating. Adjusting the concentration of the oxidized cellulose pulp fibers may be done e.g. when the consistency of the disintegrated oxidized nanofibrillar cellulose hydrogel obtained would otherwise be too thick for feeding or pumping. The concentration may be adjusted e.g. to a concentration that is equal to or less than 3% (w/w) or 2% (w/w).

Disintegrating the oxidized cellulose pulp fibers to obtain an oxidized nanofibrillar cellulose hydrogel results in the fibrillation of the oxidized cellulose pulp fibers.

The term fibrillation may be used interchangeably with expression disintegration, and generally refers to disintegrating the oxidized cellulose pulp fibers mechanically by work applied to the fibers, where cellulose fibrils are liberated from the fibers or fiber fragments. The work may be based on various effects, like grinding, crushing or shearing, or a combination of these, or another corresponding action that delaminates the cell walls of the fibers and liberates fibrils. The energy taken by the refining work is normally expressed in terms of energy per processed raw material quantity, in units of e.g. kWh/kg, MWh/ton, or units proportional to these. Mechanical disintegrating of the cellulose raw material may be carried out with any suitable equipment such as a refiner, grinder, disperser, homogenizer, colloider, friction grinder, pin mill, rotor-rotor dispergator, ultrasound sonicator, fluidizer such as microfluidizer, macrofluidizer or fluidizer-type homogenizer. The disintegrating may be performed at conditions wherein water is sufficiently present to prevent the formation of bonds between the fibers. The oxidized NFC hydrogel may be manufactured in a consistency of from 0.05 to 10% w/w, such as from 0.1 to 4% w/w, such as from 0.12 to 1.2% w/w, said consistencies being convenient for the fibrillation and the handling of the oxidized NFC hydrogel.

The means or equipment for disintegrating cellulose pulp fibers may also be decontaminated or sterilized, i.e. essentially sterile.

An oxidized nanofibrillar cellulose hydrogel obtainable by the process may already be essentially sterile after disintegrating, as all steps of the process after the oxidizing are performed under aseptic conditions. However, it is also possible to further reduce the number of viable micro-organisms in the oxidized nanofibrillar cellulose hydrogel after disintegrating.

Therefore the process may comprise subjecting the oxidized nanofibrillar cellulose hydrogel to a further sterilization treatment for reducing the number of viable micro-organisms in the oxidized nanofibrillar cellulose hydrogel. The further sterilization treatment may be capable of reducing the number of viable micro-organisms by a factor of at least $10^2$, at least $10^3$, at least $10^4$, at least $10^5$, or at least $10^6$.

The further sterilization treatment may also be capable of reducing the number of viable micro-organisms by at least a factor that is calculated as $10^{12}$ subtracted by the factor of reducing the number of viable micro-organisms obtainable by the process steps preceding the further sterilization treatment. In other words, if the steps of the process preceding the further sterilization treatment are capable of reducing the number of viable micro-organisms by a factor of $10^8$, the further sterilization treatment may be capable of further reducing the number of viable micro-organisms by a factor of at least $10^{12}$-$10^{8}$=$10^{4}$, i.e. by a factor of at least $10^{4}$.

Various suitable further sterilization treatments may be used.

The further sterilization treatment may comprise subjecting the oxidized nanofibrillar cellulose hydrogel to non-ionizing or ionizing radiation. The non-ionizing radiation may be e.g. ultraviolet light irradiation. The ionizing radiation may be e.g. irradiation with gamma rays, X-rays, or subatomic particles such as electrons. Small doses, such as doses in the range of about 1-50 kGy, or about 2-25 kGy, may be sufficient.

The further sterilization treatment may comprise subjecting the oxidized nanofibrillar cellulose hydrogel to a heat treatment, wherein the heat treatment comprises keeping the oxidized nanofibrillar cellulose hydrogel at a temperature of at least 130° C. for at least 0.5 seconds.

Treating the nanofibrillar cellulose hydrogel at a rather high temperature for a rather short period of time has the effect of reducing or eliminating the number of viable micro-organisms in the hydrogel without compromising, in an adverse extent, other properties, such as the viscosity, of the nanofibrillar cellulose hydrogel, which would affect its suitability to be further used in e.g. cosmetic or pharmaceutical products or devices. The present inventor of found out that the heat treatment at a high temperature for a short period of time may not affect the viscosity of the hydrogel in a similar manner as e.g. autoclaving does.

The operating pressures are to be selected so that the nanofibrillar cellulose hydrogel is not boiling in the used temperature. The pressure may be higher than vapour pressure of water.

The nanofibrillar cellulose hydrogel to be subjected to heat treatment may have a dry matter content of at least 0.6 weight-%, or at least 0.7 weight-%, or at least 0.8 weight-%, or at least 0.9 weight-%, or at least 1 weight-%. The nanofibrillar cellulose hydrogel to be subjected to heat treatment may also have a dry matter content of at most 4 weight-%, or at most 3 weight-%, or at most 2 weight-%. The nanofibrillar cellulose hydrogel to be subjected to heat treatment may also have a dry-matter content of 0.6-4 weight-%, or 0.7-3 weight-%, or 0.8-3 weight-%, or 0.9-2 weight-%. Such hydrogels may be more resistant to possible adverse effects of the heat treatment to the properties of the hydrogel.

The heat treatment may comprise heating the nanofibrillar cellulose hydrogel up to a temperature of at least 130° C. in at most 5 seconds; and keeping the nanofibrillar cellulose hydrogel at a temperature of at least 130° C. for at least 0.5 seconds.

The heat treatment may comprise heating the nanofibrillar cellulose hydrogel up to a temperature of at least 133° C. in at most 5 seconds; and keeping the nanofibrillar cellulose hydrogel at a temperature of at least 133° C. for at least 0.5 seconds.

The heat treatment may comprise heating the nanofibrillar cellulose hydrogel up to a temperature of at least 135° C. in at most 5 seconds; and keeping the nanofibrillar cellulose hydrogel at a temperature of at least 135° C. for at least 0.5 seconds.

The process may comprise, after the heat treatment, the step of cooling the nanofibrillar cellulose hydrogel to a temperature of below 30° C. in at most 120 seconds. The cooling has the effect of preventing evaporation of water from the nanofibrillar cellulose hydrogel after it has been packed for storage or for further use.

The heat treatment may comprise keeping the nanofibrillar cellulose hydrogel at a temperature of 130-150° C. for at most 30 seconds, or at most 15 seconds, or at most 4 seconds, or for 1-2 seconds. In one embodiment the heat treatment comprises keeping the nanofibrillar cellulose hydrogel at a temperature of 130-150° C. for at most 30 seconds. In one embodiment the heat treatment comprises keeping the nanofibrillar cellulose hydrogel at a temperature of 130-150° C. for at most 15 seconds. In one embodiment the heat treatment comprises keeping the nanofibrillar cellulose hydrogel at a temperature of 130-150° C. for at most 4 seconds. In one embodiment, the heat treatment comprises keeping the nanofibrillar cellulose hydrogel at a temperature of 130-150° C. for 1-2 seconds.

In an embodiment, the heat treatment comprises keeping the nanofibrillar cellulose hydrogel at a temperature of 133-150° C. for at most 30 seconds, or at most 15 seconds, or at most 4 seconds, or for 1-2 seconds. In an embodiment the heat treatment comprises keeping the nanofibrillar cellulose hydrogel at a temperature of 133-150° C. for at most 30 seconds. In one embodiment the heat treatment comprises keeping the nanofibrillar cellulose hydrogel at a temperature of 133-150° C. for at most 15 seconds. In an embodiment the heat treatment comprises keeping the nanofibrillar cellulose hydrogel at a temperature of 133-150° C. for at most 4 seconds. In an embodiment the heat treatment comprises keeping the nanofibrillar cellulose hydrogel at a temperature of 133-150° C. for 1-2 seconds.

In an embodiment, the heat treatment comprises keeping the nanofibrillar cellulose hydrogel at a temperature of 135-150° C. for at most 30 seconds, or at most 15 seconds, or at most 4 seconds, or for 1-2 seconds. In an embodiment the heat treatment comprises keeping the nanofibrillar cellulose hydrogel at a temperature of 135-150° C. for at most 30 seconds. In an embodiment the heat treatment comprises keeping the nanofibrillar cellulose hydrogel at a temperature of 135-150° C. for at most 15 seconds. In an embodiment the heat treatment comprises keeping the nanofibrillar cellulose hydrogel at a temperature of 135-150° C. for at most 4 seconds. In an embodiment the heat treatment comprises keeping the nanofibrillar cellulose hydrogel at a temperature of 135-150° C. for 1-2 seconds.

The heat treatment may be carried out by contacting the nanofibrillar cellulose hydrogel with steam. The heat treatment can be carried out by so-called direct heating methods, such as steam injection or steam infusion, wherein the nanofibrillar cellulose hydrogel is mixed with heating steam. The heating apparatus may also be configured to contact the nanofibrillar cellulose hydrogel with steam.

The heat treatment may be carried out by a so-called indirect heating method, using e.g. a plate heat exchanger or a tubular heat exchanger, which keep the nanofibrillar cellulose hydrogel and the heating medium separate with a barrier between them. The heating apparatus may be a heat exchanger.

The heat treatment and/or the step of cooling the nanofibrillar cellulose hydrogel may be carried out in at least one heat exchanger.

The viscosity of the oxidized nanofibrillar cellulose hydrogel may, after the further sterilization treatment, such as heat treatment, differ at most 50%, or at most 30%, or at most 10%, or at most 5%, when conducted in at least 0.6% w/w concentration, from the viscosity of the nanofibrillar cellulose hydrogel before the further sterilization treatment and when the viscosity after the heat treatment is measured in the same dry matter content of at least 0.6 weight. I.e. the viscosity is measured in the same dry matter content before and after the further sterilization treatment.

The process may further comprise packaging the oxidized nanofibrillar cellulose hydrogel into units. The packaging may also be done under aseptic conditions, i.e. aseptically. The oxidized nanofibrillar cellulose hydrogel may be packaged into units of e.g. 1 g, 5 5, 10 g or 100 g, for instance in ampules or other suitable containers. The oxidized nanofibrillar cellulose hydrogel may also be packaged into multiwell plates. The units may be packaged in containers that are decontaminated or sterilized, i.e. essentially sterile.

The number of viable micro-organisms may be reduced during the process for preparing an oxidized nanofibrillar cellulose hydrogel by a factor of at least $10^3$, or at least $10^6$, or at least $10^7$, or at least $10^8$, or at least $10^9$, or at least $10^{10}$, or or at least $10^{11}$, or at least $10^{12}$. This factor may be calculated on the basis of the number of viable micro-organisms originally present prior to oxidizing, i.e. viable micro-organisms present in the cellulose pulp fibers, any aqueous solution in which the cellulose pulp fibers are mixed or dispersed, and the heterocyclic nitroxyl radical as a catalyst prior to the addition of the hypochlorite; and on the basis of the number of viable micro-organisms present in the oxidized nanofibrillar cellulose hydrogel obtainable by the process.

An oxidized nanofibrillar cellulose hydrogel obtainable by the process according to one or more embodiments is disclosed. The oxidized nanofibrillar cellulose hydrogel obtainable by the process according to one or more embodiments may be sterile or essentially sterile. It may also have a viscosity of at least 2000 mPa·s, or at least 12000 mPa·s, or at least 20000 mPa·s, or 2000-40000 mPa·s, or 12000-30000 mPa·s, or 15000-25000 mPa·s, or 20000-40000 mPa·s, as measured at a 0.8% (w/w) concentration of the nanofibrillar cellulose in water with a Brookfield viscometer at a temperature of 20° C., with a vane spindle and a measuring speed of 10 rpm.

An oxidized nanofibrillar cellulose hydrogel is disclosed, wherein the oxidized nanofibrillar cellulose hydrogel is sterile, or essentially sterile, and has a viscosity of at least 2000 mPa·s, or at least 12000 mPa·s, or at least 20000 mPa·s, or 2000-40000 mPa·s, or 12000-30000 mPa·s, or 15000-25000 mPa·s, or 20000-40000 mPa·s, as measured at a 0.8% (w/w) concentration of the oxidized nanofibrillar cellulose in water with a Brookfield viscometer at a temperature of 20° C., with a vane spindle and a measuring speed of 10 rpm.

The so-called Brookfield viscosity measurement can be performed in the following manner: A vane spindle (number 73) is selected and the Brookfield-viscosity measuring apparatus (Brookfield RVDV-III) is started. A sample of the nanofibrillar cellulose is diluted to a concentration of 0.8% by weight in water and mixed for 10 minutes using a propel mixer at 700-800 rpm. No ultrasound mixing is used. The diluted sample mass is added to a 250 ml beaker and the temperature is adjusted to 20° C.±1° C., heated if necessary and mixed. The spindle is inserted in the beaker and measuring is started. 300 points are registered starting with 0.5 rpm speed, then 300 points with 5 rpm and 10 rpm, and 100 points with 50 rpm and 100 rpm speeds. Relative viscosity is measured from each sample mass twice. Mean value and standard deviation are calculated for each sample, from results obtained from parallel measurements during the last 5 seconds.

The process according to one or more embodiments allows for producing an oxidized nanofibrillar cellulose hydrogel that is essentially sterile but the properties of which, such as high viscosity and turbidity, do not suffer, as opposed e.g. to oxidized nanofibrillar cellulose hydrogel that has been autoclaved.

The oxidized nanofibrillar cellulose hydrogel may have a turbidity of at most 90 NTU, or at most 60 NTU, or at most 40 NTU, or 1 to 90 NTU, or 1 to 60 NTU, or 10 to 40 NTU, as measured at 0.1% (w/w) concentration of the nanofibrillar cellulose in water.

A turbidometric method based on nephelometry (90° angle between light source and detector) can be used for measuring the turbidity of samples. HACH P2100 Turbidometer, with a 50 ml measuring vessel may be used for turbidity measurements. The calibration of the apparatus is checked and controlled with standard calibration bottles/samples. The dry matter of the nanofibrillar cellulose sample is determined and 0.5 g of the sample, calculated as dry matter, is loaded in the measuring vessel, which is filled with tap water to 500 g and vigorously mixed by shaking for about 30 s. Without delay the aqueous mixture is divided into 5 measuring vessels, which are inserted in the turbidometer. Three measurements on each vessel are carried out. Mean value and standard deviation are calculated for each sample.

The dry matter content can be determined e.g. according ISO 4119/1995, "Determination of stock concentration", with the exception that the sample is kept in an oven at a temperature of 105° C. overnight (t=16 h) and by weighing the sample before and after it is kept in the oven. One way to characterize NFC is to define both the viscosity and the turbidity. In general as the fibrillation degree increases, the viscosity increases and at the same time the turbidity decreases. This happens, however, until a certain point. When the fibrillation is further continued, the fibrils begin finally to break and cannot form a strong network any more. Therefore after this point both the turbidity and the viscosity begin to decrease. Such a grade may be called a low viscosity oxidized grade, and the Brookfield viscosity thereof may range from 2000 to 6000, or 2000 to 4000 mPas, at 0.8% (w/w).

The oxidized nanofibrillar cellulose hydrogel may comprise e.g. 0.01-4% (w/w), or 0.1-2.5% (w/w), or 0.2-1.5% (w/w), or 0.2-1.2% (w/w), of oxidized nanofibrillar cellulose.

The oxidized nanofibrillar cellulose may comprise e.g. at least 500 µmol/g, or at least 800 µmol/g, or 500-1500 µmol/g, or 800-1200 µmol/g of COOH residues based on the dry weight of the oxidized nanofibrillar cellulose. The oxidation level may be determined from the oxidized pulp, but the oxidation level may be considered to be the same or essentially the same based on the dry weight of the oxidized nanofibrillar cellulose.

The oxidation level may be determined by mixing bleached pulp with a $ClO_2$ water solution in a closed vessel. The pulp is mixed with water (pulp consistency 1-4%) and transferred to a Büchi reactor (mixing, temperature 25-50° C., volume of pulp solution 1-1.2 dm3). The activated TEMPO solution and NaClO is added to the Büchi reactor. pH is adjusted by 1 M NaOH and automatic titrator after a rapid pH decrease at the beginning of the oxidation. The oxidation rate is investigated by active chlorine titration until all HOCl is consumed. The pulp is washed through wire cloth. Carboxylate content is analyzed from the washed pulp samples by conductometric titration.

The conductometric titration may be performed by converting the pulp samples to their protonated form prior to the titration. First, the pH of the pulp suspension is adjusted to 2 with 1M HCl. The solution is left to stabilize for 0.5 hours, after which the pulp is washed with water until the conductivity of the slurry is less than 5 µS/cm. Approximately 1 g (dry matter content) pulp is weighed in a 600 ml Erlenmeyer flask. Carbon dioxide is removed by a vacuum from the purified water. The carbon dioxide-free water is used both during the titration and the preparation of the reagent solution. The pulp sample is dispersed in 498.5 ml of water. Then, 1 ml of 0.1 M HCl and 0.5 ml of 0.5 M NaCl is added to the Erlenmeyer flask. Titration is executed under argon gas atmosphere using an automatic titrator (e.g. Metrohm 751 GPD Titrino) together with Tiamo 1.2.1. software.

The sterile oxidized nanofibrillar cellulose hydrogel may comprise fewer than $10^{-1}$, or fewer than $10^{-2}$, or fewer than $10^{-3}$, or fewer than $10^{-4}$, or fewer than $10^{-5}$, or fewer than $10^{-6}$ CFU of a viable micro-organism per unit of the oxidized nanofibrillar cellulose hydrogel. A unit may be e.g. 1 g, 5 g, 10 g or 100 g of the oxidized nanofibrillar cellulose hydrogel, for instance in an ampule. The unit may also be a multiwell plate containing the oxidized nanofibrillar cellulose hydrogel in one or more wells, or a single well of a multiwell plate.

The sterile oxidized nanofibrillar cellulose hydrogel may comprise fewer than $10^{-1}$, or fewer than $10^{-2}$, or fewer than $10^{-3}$, or fewer than $10^{-4}$, or fewer than $10^{-5}$, or fewer than $10^{-6}$ CFU of a viable micro-organism per gram of the oxidized nanofibrillar cellulose hydrogel.

The sterile oxidized nanofibrillar cellulose hydrogel may comprise fewer than $10^{-1}$, or fewer than $10^{-2}$, or fewer than $10^{-3}$, or fewer than $10^{-4}$, or fewer than $10^{-5}$, or fewer than $10^{-6}$ CFU of a viable micro-organism for a unit of 1 gram of the oxidized nanofibrillar cellulose hydrogel.

The oxidized nanofibrillar cellulose hydrogel according to one or more embodiments for use in therapy is disclosed.

The use of the oxidized nanofibrillar cellulose hydrogel according to one or more embodiments in a cosmetic product is disclosed.

A growth medium for cell culture comprising the oxidized nanofibrillar cellulose hydrogel according to one or more embodiments is disclosed.

The use of the oxidized nanofibrillar cellulose hydrogel according to one or more embodiments in cell culture is disclosed.

A system for producing an oxidized nanofibrillar cellulose hydrogel is disclosed, wherein the system comprises a reaction apparatus for oxidizing cellulose pulp fibers in the presence of hypochlorite as an oxidant and a heterocyclic nitroxyl radical as a catalyst; and a disintegration apparatus for disintegrating the oxidized cellulose pulp fibers to obtain an oxidized nanofibrillar cellulose hydrogel;

wherein the disintegration apparatus and any optional components of the system that are configured to be in contact with the oxidized cellulose pulp fibers and/or oxidized nanofibrillar cellulose are configured to operate under aseptic conditions.

The reaction apparatus may be e.g. a reactor or container and may comprise e.g. a mixer or impeller for mixing the cellulose pulp fibers, the hypochlorite and the catalyst. The reaction apparatus may also comprise means for feeding the hypochlorite into the reactor or container.

The disintegration apparatus may be e.g. a refiner, grinder, disperser, homogenizer, colloider, friction grinder, pin mill, rotor-rotor dispergator, ultrasound sonicator, or a fluidizer such as microfluidizer, macrofluidizer or fluidizer-type homogenizer.

The aseptic conditions may correspond to ISO 14644-1 cleanroom standard ISO 5, or to ISO 4, or to ISO 3, or to ISO 2, or to ISO 1.

The system may comprise a washing apparatus for washing the oxidized cellulose pulp fibers. The washing apparatus may comprise e.g. a filter press for thickening the oxidized cellulose pulp fibers dispersed in the mixture and a pulper for redispersing the oxidized cellulose pulp fibers in water.

The system may also comprise a sterilization apparatus for a further sterilization treatment for reducing the number of viable micro-organisms in the oxidized nanofibrillar cellulose hydrogel by a factor of at least $10^3$.

The sterilization apparatus may comprise e.g. a source of non-ionizing radiation, such as an ultraviolet lamp, or a source of ionizing radiation, such as a source of gamma rays, X-rays or of subatomic particles.

The sterilization apparatus may also comprise a heating apparatus. The heating apparatus may be configured to heat the oxidized nanofibrillar cellulose up to a temperature of at least 130° C. in at most 0.5 seconds. The heating apparatus may be e.g. a heat exchanger.

The system may comprise a cooling apparatus for cooling the oxidized nanofibrillar cellulose hydrogel to a temperature of below 30° C. in at most 120 seconds. The cooling apparatus may be e.g. a heat exchanger. The system may also comprise a cooling apparatus, which is configured to cool the nanofibrillar cellulose hydrogel to a temperature of below 30° C. in at most 120 seconds.

The heating apparatus and the cooling apparatus may be the same apparatus or two different apparatuses.

The system may further comprise a packaging apparatus for packaging the oxidized nanofibrillar cellulose hydrogel. The packaging apparatus may be suitable for aseptic packaging e.g. in ampules.

Any or all components of the system that are configured to be in contact with the oxidized cellulose pulp fibers and/or oxidized nanofibrillar cellulose may be decontaminated and configured to provide uncompromised, continuous isolation of their interior from the external environment. The optional components of the system that are configured to be in contact with the oxidized cellulose pulp fibers and/or oxidized nanofibrillar cellulose may include e.g. the disintegration apparatus, the washing apparatus, the sterilization apparatus, the packaging apparatus, one or more pumps and connections between said apparatuses.

The system may be configured to exclude external contamination from the its interior by accomplishing material transfer via aseptic connection to auxiliary equipment, rather than via openings to the surrounding environment. Such a system may be configured to remain sealed throughout the process.

The system may also be configured to allow for the continuous or semi-continuous ingress and/or egress of materials during the process through one or more openings. The openings may be configured (e.g. using continuous overpressure) to exclude the entry of external contamination into the system.

The embodiments of the invention described hereinbefore may be used in any combination with each other. Several of the embodiments may be combined together to form a further embodiment of the invention. A process, a hydrogel, a system, or a use, to which the invention is related, may comprise at least one of the embodiments described hereinbefore.

Technical effects of one or more embodiments include that the number of viable microoganisms may be significantly reduced in oxidized nanofibrillar cellulose hydrogel without compromising the properties, such as viscosity, of the hydrogel, which would affect its suitability to be further used in e.g. cosmetic or pharmaceutical products or devices.

Technical effects of one or more embodiments include that an oxidized nanofibrillar cellulose hydrogel may be provided for use in pharmaceutical or cosmetic applications.

EXAMPLES

Reference will now be made in detail to the embodiments, an example of which is illustrated in the accompanying drawing.

The description below discloses some embodiments in such a detail that a person skilled in the art is able to utilize the invention based on the disclosure. Not all steps of the embodiments are discussed in detail, as many of the steps will be obvious for the person skilled in the art based on this specification.

For reasons of simplicity, item numbers will be maintained in the following exemplary embodiments in the case of repeating components.

Figure 1:
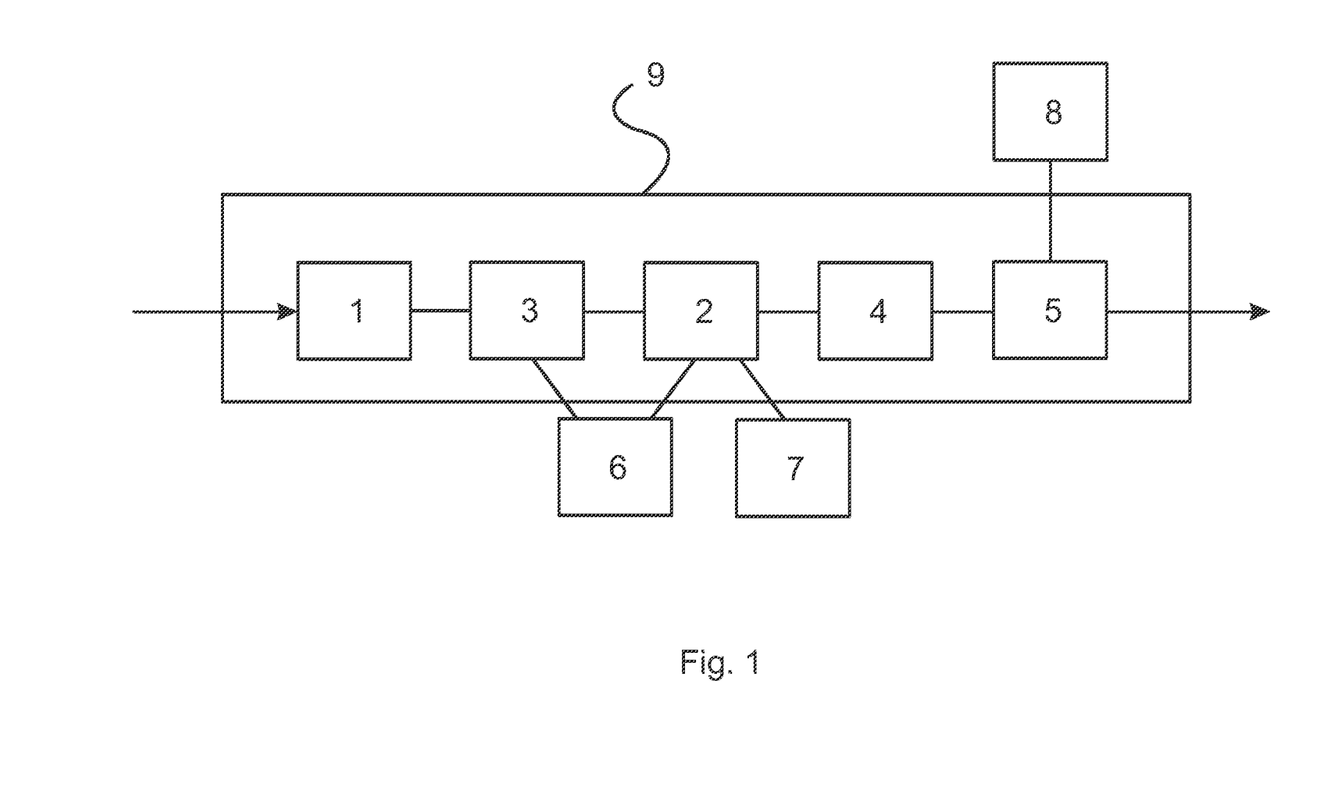
FIG. 1 illustrates a system according to one embodiment for producing an oxidized nanofibrillar cellulose hydrogel.

FIG. 1 illustrates a system according to one embodiment for producing an oxidized nanofibrillar cellulose hydrogel. The system comprises a reaction apparatus 1 for oxidizing cellulose pulp fibers in the presence of hypochlorite as an oxidant and a heterocyclic nitroxyl radical as a catalyst. The reaction apparatus 1 may be a reactor that is equipped with a mixer or impeller for mixing the components of the reaction mixture. It may also comprise means for adjusting the temperature of the reaction mixture, such as heating means (heater) or cooling means (cooler).

The oxidized cellulose pulp fibers may be provided to a washing apparatus 3 for washing the oxidized cellulose pulp fibers. Sterilized water (or other sterilized aqueous solution) may be provided to the washing apparatus 3 from a source of sterile water 6. The sterilized water may be e.g. autoclaved to ensure it is essentially sterile.

The system also comprises a disintegration apparatus 2 for disintegrating the oxidized cellulose pulp fibers to obtain an oxidized nanofibrillar cellulose hydrogel. The disintegration apparatus 2, such as a fibrillation unit, is configured to fibrillate the oxidized cellulose pulp fibers. Suitable disintegration apparatuses may be e.g. a fluidizer, a homogenizer or other apparatuses that are configured to exert strong shear, turbulence, impact or pressure forces on the oxidized cellulose pulp fibers. If desired, sterilized water may be provided from the source of sterile water to the disintegration apparatus 2 to dilute the hydrogel obtainable in the disintegration apparatus 2. Vent air may be provided to the disintegration apparatus 2 from a source of sterilized air 7. The source of sterilized air 7 may comprise e.g. one or more filters that are capable of removing particular matter and viable micro-organisms from the air.

The oxidized nanofibrillar cellulose hydrogel obtained in the disintegration apparatus 2 may be provided to a sterilization apparatus 4 for further sterilization treatment of the oxidized nanofibrillar cellulose hydrogel. The sterilization apparatus 4 may be e.g. a heating apparatus, wherein the hydrogel is subjected to a heat treatment. The heating apparatus may be configured to keep the oxidized nanofibrillar cellulose hydrogel at a temperature of at least 130° C. for at least 0.5 seconds, for reducing the number of viable micro-organisms in the oxidized nanofibrillar cellulose hydrogel. The sterilization apparatus 4 may alternatively comprise e.g. a source of non-ionizing radiation, such as an ultraviolet lamp, or a source of ionizing radiation, such as a source of gamma rays, X-rays or of subatomic particles.

The oxidized nanofibrillar cellulose hydrogel that has been subjected to the further sterilization treatment is packaged in a packaging apparatus 5 for packaging the oxidized nanofibrillar cellulose hydrogel. The packaging apparatus 5 is suitable for aseptic packaging e.g. into ampules, bottles, multiwell plates or other containers. They may be sterilized in a sterilization apparatus 8 for sterilizing containers for packaging the oxidized nanofibrillar cellulose hydrogel.

The system also comprises aseptic fluid connections configured to convey material, such as reaction mixture containing the oxidized cellulose pulp fibers and the oxidized nanofibrillar cellulose hydrogel between parts of the system.

The washing apparatus 3, the disintegration apparatus 2, the sterilization apparatus 4 and the packaging apparatus 5 are configured to operate under aseptic conditions. They may be decontaminated by sterilization treatments prior to operation of the system. Fluid connections between components of the system that are configured to be in contact with or to convey material or fluid that is to be in contact with the oxidized cellulose pulp fibers and/or the oxidized nanofibrillar cellulose hydrogel are via aseptic connections.

The system further comprises a cleanroom 9 or another similar barrier for providing an environment that has a controlled level of contamination by micro-organisms and particles. Such a system may be configured to remain sealed throughout the process. The cleanroom 9 may be configured to exclude external contamination from the its interior by accomplishing material transfer via aseptic connection to auxiliary equipment, rather than via openings to the surrounding environment.

The cleanroom 9 may also be configured to allow for the continuous or semi-continuous ingress and/or egress of materials during the process through one or more openings. The openings may be configured (e.g. using continuous overpressure) to exclude the entry of external contamination into the system.

After the oxidized nanofibrillar cellulose hydrogel is packaged aseptically into suitable containers that preserve its sterility, it may be removed from the cleanroom 9.

Example 1—Preparing a Sterile Oxidized Nanofibrillar Cellulose Hydrogel by Autoclaving A comparative example was provided by oxidizing cellulose pulp fibers to an oxidation level of 850 μmol COOH/g pulp using sodium hypochlorite and TEMPO as the catalyst. The oxidized cellulose pulp fibers were disintegrated into fibrils using an Atrex® homogenisator at a concentration of 2.5% (w/w) based on dry weight of the oxidized cellulose pulp fibers. The anionic nanofibrillar cellulose hydrogel thus obtained was diluted to a concentration of 1.5% by mixing for 30 seconds using a Bamix® mixer. The diluted hydrogel was autoclaved at a temperature of 121° C. for minutes. During the warmup before and the cooling after the autoclaving temperature, the temperature exceeded 80° C. for about 30 minutes.

The Brookfield viscosity of the hydrogel was measured before and after autoclaving.

Viscosity measurements of the nanofibrillar cellulose hydrogels were carried out as follows. A vane spindle (number 73) was selected and the Brookfield-viscosity measuring apparatus (Brookfield RVDV-III) was started. A sample of the nanofibrillar cellulose hydrogel was diluted to a concentration of 0.5% by weight in water and mixed for 10 min using a propel mixer 700-800 rpm. No ultrasound mixing was used for modified grades. The diluted sample mass was added to a 250 ml beaker and the temperature was adjusted to 20° C.±1° C., pH 7, heated if necessary and mixed. The spindle was inserted in the beaker and measuring was started. The program registered 300 points starting with 0.5 rpm speed, then 300 points with 5 rpm and 10 rpm, and 100 points with 50 rpm and 100 rpm speeds. Relative viscosity was measured from each sample mass twice. Mean value and standard deviation were calculated for each sample, from results obtained from parallel measurements during last 5 seconds.

For rheological measurement the following method was used. Measurement was carried out with a stress controlled rotational rheometer (ARG2, TA instruments, UK) equipped with four-bladed vane geometry. Samples were diluted with deionized water (200 g) to a concentration of 0.5 wt % and mixed with Waring Blender (LB20E*, 0.5 l) 3×10 sec (20 000 rpm) with short break between the mixing. Rheometer measurement was carried out for the sample, pH 7. The diameters of the cylindrical sample cup and the vane were 30 mm and 28 mm, respectively, and the length was 42 mm. The steady state viscosity of the hydrogels was measured using a gradually increasing shear stress of 0.001-1000 Pa. After loading the samples to the rheometer they were allowed to rest for 5 min before the measurement was started, room temperature. The steady state viscosity was measured with a gradually increasing shear stress (proportional to applied torque) and the shear rate (proportional to angular velocity) was measured. The reported viscosity (=shear stress/shear rate) at a certain shear stress was recorded after reaching a constant shear rate or after a maximum time of 2 min. The measurement was stopped when a shear rate of 1000 s-1 was exceeded.

Dry matter content was measured by keeping a sample in an oven at a temperature of 105° C. overnight (t=16 h) and by weighing the sample before and after it was kept in the oven. The weighing process was conducted following the standard ISO 4119/1995, "Determination of stock concentration", with the difference that the time was 16 h.

Figure 2:
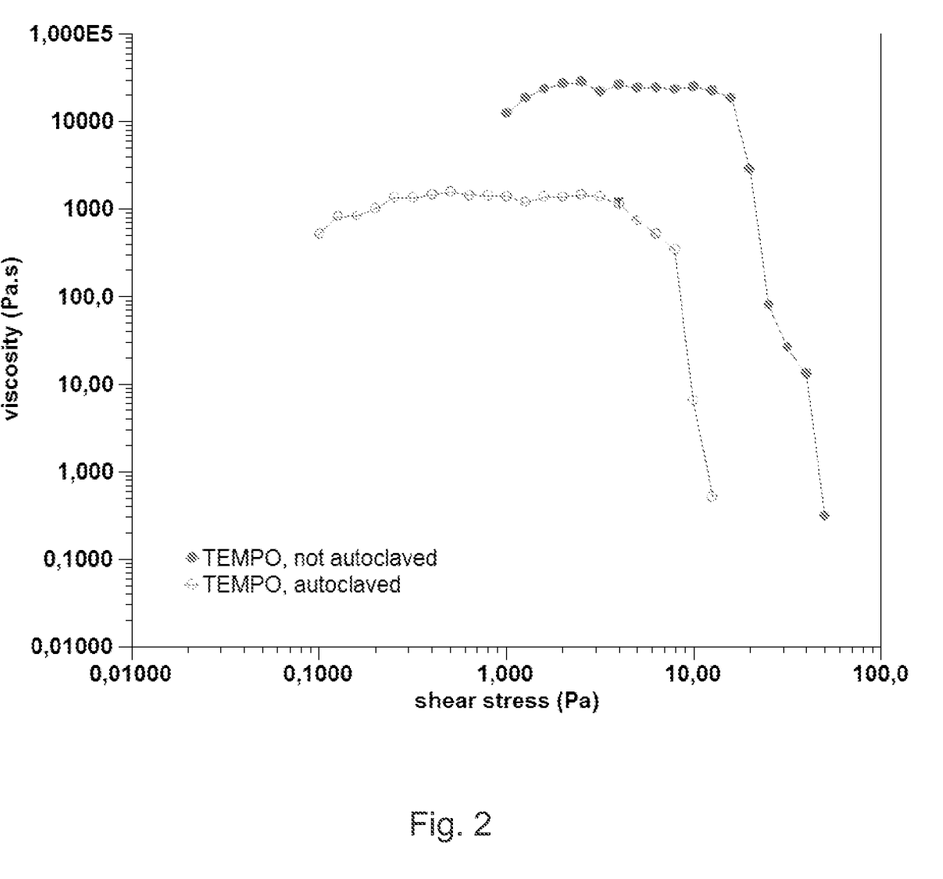
FIG. 2 shows the results of viscosity measurements of autoclaved oxidized nanofibrillar cellulose hydrogel.

FIG. 2 demonstrates the effect of autoclaving on oxidized nanofibrillar cellulose hydrogel. The viscosity of the autoclaved oxidized nanofibrillar cellulose hydrogel was clearly lower than of a corresponding hydrogel that was not autoclaved. A clear yield stress cutoff is also not observed.

Example 2—Preparing a Sterile Oxidized Nanofibrillar Cellulose Hydrogel Under Aseptic Conditions TEMPO oxidized nanofibrillar cellulose hydrogel was produced by dispersing baled cellulose for 30 min in a pulper at a concentration of 4% (w/w). The dispersion was placed overnight in a reaction tank, after which oxidization chemicals were added in the reaction tank and the oxidization was allowed to proceed for 6 hours. The obtained mixture was thickened to a concentration of 35% dry matter in a filter press for 2-4 hours. The thickened mixture was redispersed to 3-5% dry matter in a pulper. The redispersed mixture was thickened again to a concentration of about 20% dry matter in a filter press and redispersed to a concentration of 2% dry matter in a pulper. The redispersed mixture was fibrillated using an Atrex® homogenisator for two cycles. The water used for redispersing was non-sterile milliQ water.

The effect of various process steps on microbiological quality of the TEMPO oxidised nanofibrillar cellulose was studied by sampling the product in the beginning and in the end of each process step. The samples were stored refrigerated before the analysis.

The number of colony-forming units per gram of nanofibrillar cellulose hydrogel was measured by preparing a dilution series of the hydrogel and by plating the dilution series on separate Petrifilm plates (3M) for aerobic bacteria (aerobic plate count) and for yeasts and moulds. The plates for aerobic bacteria were allowed to grow at 37° C. for 2 days and the plates for yeasts and moulds at 30° C. for 3-5 days, after which the colonies were counted. The number of colony-forming units of aerobic heterotrophs was determined by culturing the sample on plate count agar at a temperature of 37° C. for three (3) days.

The count of aerobic heterotrophic bacteria in the pulp at arrival was >$10^5$ CFU/g (see Table 1). The microbiological load was decreased during the chemical oxidization treatment and no microbes were detected in the product during the 1st thickening after TEMPO oxidation or in the thickened product immediately before redispersion. During redispersion the aerobic heterotrophic bacterial count increased to $10^3$-$10^4$ CFU/g and was further increased to $10^6$ CFU/g during the 3 d storage of the product after the $2^{nd}$ thickening.

TABLE 1

Counts of aerobic heterotrophic bacteria, anaerobes and moulds in TEMPO oxidised nanofibrillar cellulose during processing.

| Sample | Heterotrophic bacteria CFU/g | Anaerobes CFU/g | Moulds CFU/g |
|---|---|---|---|
| Pulp (at arrival) | $4.70 \times 10^5$ | 20 | <10 |
| Pulp (beginning of processing) | $5.85 \times 10^5$ | $1.35 \times 10^2$ | <10 |
| Chemical treatment | | Not sampled | |
| $1^{st}$ thickening, start (= end of chemical treatment) | <10 | <10 | <10 |
| $1^{st}$ thickening, end | <10 | <10 | <10 |
| $1^{st}$ thickening before redispersion | <10 | <10 | <10 |
| Redispersed | $3.00 \times 10^4$ | <10 | <10 |
| $2^{nd}$ thickening, start | $7.80 \times 10^2$ | <10 | <10 |
| $2^{nd}$ thickening, end | $1.70 \times 10^5$ | <10 | 10 |
| $2^{nd}$ thickening before redispersion | $1.29 \times 10^6$ | $5.30 \times 10^2$ | <10 |
| Redispersed | $1.39 \times 10^5$ | $1.10 \times 10^2$ | <10 |

Example 3—Preparing a Sterile Oxidized Nanofibrillar Cellulose Hydrogel Under Aseptic Conditions The experiment described in Example 2 was repeated, with the exception that the tanks and pipelines were cleaned and disinfected more carefully and that prolonged storage of intermediate products was avoided. As a consequence of the improved process hygiene, the microbiological quality of the product was significantly improved (see Table 2). The bacterial counts of the pulp in the beginning of processing were on the same level as in the previous run. The counts in tap water used for diluting were below the detection limit. No bacteria were detected in the product during the first thickening after the chemical treatment and bacterial counts remained low (50-100 CFU/g) during redispersion and the second thickening as well. The final product was not analysed, as a biocide was added to the product before fibrillation.

TABLE 2

Counts of aerobic heterotrophic bacteria, anaerobes and moulds in TEMPO oxidised nanofibrillar cellulose during processing.

| | Sample | Heterotrophic bacteria CFU/g | Anaerobes CFU/g | Moulds CFU/g |
|---|---|---|---|---|
| Pulp | Pulp (at arrival) | $4.25 \times 10^5$ | 25 | <10 |
| | Pulp (tank K5) | $2.85 \times 10^5$ | 25 | <10 |
| | Pulp (tank K9) | $7.20 \times 10^5$ | <10 | <10 |
| Water | Tap water | <10 | <10 | <10 |
| Batch 1 | Chemical treatment | | Not sampled | |
| | 1st thickening | <10 | <10 | <10 |
| | Redispersed | 350 | <10 | <10 |
| | 2nd thickening, start | 100 | <10 | <10 |
| | 2nd thickening, end | 100 | <10 | <10 |
| Batch 2 | 1st thickening | <10 | <10 | 30 |
| | Redispersed | 50 | <10 | 20 |
| | 2nd thickening, start | <100 | <10 | 10 |
| | 2nd thickening, end | 100 | <10 | 10 |

It is obvious to a person skilled in the art that with the advancement of technology, the basic idea of the invention may be implemented in various ways. The invention and its embodiments are thus not limited to the examples described above; instead they may vary within the scope of the claims.

The invention claimed is:

1. A process for producing an oxidized nanofibrillar cellulose hydrogel, wherein the process comprises:
    a) oxidizing cellulose pulp fibers in the presence of hypochlorite as an oxidant and a heterocyclic nitroxyl radical as a catalyst to form sterile or essentially sterile oxidized cellulose pulp fibers, wherein a total amount of hypochlorite ions fed is at least 2.0 mmol/g based on dry weight of the cellulose pulp fibers, and wherein the oxidizing is conducted for 1 to 8 hours, wherein hypochlorite ions are present during at least a period of time during the oxidizing at a concentration level of 0.5 to 5.0 g/l, the concentration level being calculated based on the total volume of a mixture of the hypochlorite ions, the cellulose pulp fibers, and an aqueous solution in which the oxidizing takes place;
    b) adjusting the concentration of the oxidized cellulose pulp fibers to equal to or less than 3% (w/w); and
    c) disintegrating the oxidized cellulose pulp fibers to obtain a sterile or essentially sterile oxidized nanofibrillar cellulose hydrogel having a viscosity of at least 2000 mPa·s, as measured at a 0.8% (w/w) concentration of the nanofibrillar cellulose in water with a Brookfield viscometer at a temperature of 20° C., with a vane spindle and a measuring speed of 10 rpm,
    wherein the oxidized cellulose pulp fibers are continuously transported from one process step to a next process step in a closed environment using an aseptic connection, the aseptic conditions including using components of a system for producing the oxidized nanofibrillar cellulose hydrogel that are configured to be in contact with the oxidized cellulose pulp fibers and/or oxidized nanofibrillar cellulose that are decontaminated and provide uncompromised, continuous isolation of their interior from the external environment,
    and wherein all steps of the process after a) are performed under aseptic conditions, the conditions including meeting a cleanroom classification, according to ISO 14644-1 cleanroom standards, of at least Class ISO 8.

2. The process according to claim 1, wherein the process comprises oxidizing cellulose pulp fibers in the presence of hypochlorite as an oxidant and a heterocyclic nitroxyl radical as a catalyst at a pH of 7—10.

3. The process according to claim 1, wherein the hypochlorite is sodium hypochlorite.

4. The process according to claim 1, wherein the temperature during the oxidizing is raised to at least 30° C.

5. The process according to claim 1, wherein the process comprises washing the oxidized cellulose pulp fibers prior to disintegrating.

6. The process according to claim 1, wherein the process comprises subjecting the oxidized nanofibrillar cellulose hydrogel to a sterilization treatment to reduce the number of viable micro-organisms in the oxidized nanofibrillar cellulose hydrogel by a factor of at least $10^3$.

7. The process according to claim 6, wherein the sterilization treatment comprises subjecting the oxidized nanofibrillar cellulose hydrogel to non-ionizing or ionizing radiation.

8. The process according to claim 6, wherein the sterilization treatment comprises subjecting the oxidized nanofibrillar cellulose hydrogel to a heat treatment, wherein the heat treatment comprises keeping the oxidized nanofibrillar cellulose hydrogel at a temperature of at least 130° C. for at least 0.5 seconds.

9. The process according to claim 1, further comprising packaging the oxidized nanofibrillar cellulose hydrogel into units.

10. The process according to claim 1, wherein the number of viable micro-organisms is reduced during the process by a factor of at least 103.

11. The process of claim 1, wherein the oxidizing is conducted in a reaction apparatus, and the disintegrating takes place in a disintegration apparatus.

* * * * *